United States Patent [19]

Lee

[11] 4,048,204
[45] Sept. 13, 1977

[54] C20 AND C22 ACIDS TO PROMOTE WOUND HEALING

[75] Inventor: Kwan-Hua Lee, San Francisco, Calif.

[73] Assignee: The Regents of the University of California, Berkeley, Calif.

[21] Appl. No.: 722,247

[22] Filed: Sept. 10, 1976

Related U.S. Application Data

[63] Continuation of Ser. No. 630,483, Nov. 10, 1975, abandoned, which is a continuation of Ser. No. 498,796, Aug. 19, 1974, abandoned, which is a continuation of Ser. No. 207,623, Dec. 13, 1971, abandoned.

[51] Int. Cl.$^2$ .................. C11C 1/00; C07C 61/38
[52] U.S. Cl. ........................ 260/413; 260/410.9 V
[58] Field of Search ............ 260/413, 410.9 V, 611 V, 260/617 A; 427/318

[56] References Cited

U.S. PATENT DOCUMENTS

| | | | |
|---|---|---|---|
| 3,006,939 | 10/1961 | Pommer et al. | 260/413 |
| 3,689,667 | 9/1972 | Lee | 424/318 |
| 3,882,244 | 5/1975 | Lee | 424/318 |
| 3,966,967 | 6/1976 | Lee | 424/318 |

OTHER PUBLICATIONS

Chem. Abs., 1961, Redfearm, 7570 E.
Chem. Abs., vol. 65, Haeck et al., 3915 D.
Chem. Abs., vol. 56, Stiltz et al., 8571 C.
Chem. Abs., vol. 56, Pommer et al., 512 D.

Primary Examiner—Winston A. Douglas
Assistant Examiner—P. E. Konopka
Attorney, Agent, or Firm—Townsend and Townsend

[57] ABSTRACT

The C20 and C22 vinylogs of desmethyl retinoic acid has been found highly effective in promoting wound healing. The acid is applied to the wound as a solution, ointment or powder. These acids are the most effective yet found for healing wounds, yet do not have some of the undesirable side effects of retinoic acid.

The compounds of this invention have the following formula:

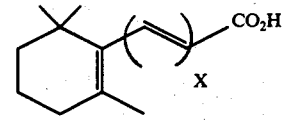

where X is an integer of from 5 to 6.

1 Claim, No Drawings

C20 AND C22 ACIDS TO PROMOTE WOUND HEALING

CROSS-REFERENCES TO RELATED APPLICATIONS

This application is a continuation of application Ser. No. 630,483, filed Nov. 10, 1975, now abandoned, which application was a continuation application of Ser. No. 498,796, filed Aug. 19, 1974, now abandoned, which in turn was a continuation application of application Ser. No. 207,623, filed Dec. 13, 1971, now abandoned.

SUMMARY OF THE INVENTION

Inflammation and mucopolysaccharide synthesis are the two important features in the early stage of wound healing. The term "wound" as used in this application means any topical lesion such as a surgical incision, accidental wound or ulcer. Aspirin inhibits both features. The healing inhibitory action of aspirin and other inflammatory agents has been demonstrated. Vitamin A increases mucopolysaccharide synthesis and it also causes inflammation. The ability of vitamin A alone to promote healing and its effectiveness in reversing the healing retardation action of aspirin is known. Retinoic acid (the acid form of vitamin A) and its salts also have been found active compounds in promoting healing. Topical application of retinoic acid or its salts reverses the healing retardation action caused by oral administration of sodium salicylate, prednisone and other inflammatory agents and topical application of salicylic acid or hydrocortisone. Topical application of retinoic acid and its salts promotes skin wound healing in rats and human beings.

It has now been found that 2,6,6,-Trimethyl-1-(10'-carboxy-deca-1', 3', 5', 7', 9'-pentaenyl) cyclohex-1-ene acid and 2,6,6,-Trimethyl-1-(12'-carboxy-dodeca-1',3',5',7',9',11'-hexaenyl) cyclohex-1-ene acid are even more effective than vitamin A or vitamin A acid for wound healing. The corresponding C16, and C18 acids have also been made and tested but they are considerably less effective than the C20 and C22 acids of the present invention. Furthermore, the acids of the present invention have been found to be considerably less toxic, even when used at high concentrations, than retinoic acid.

C20 and C22 acids promote healing. It is very practical to dust these compounds on any surgical wound or to apply either of them as a solution or in an ointment. The C20 acid is preferred.

DESCRIPTION OF THE PREFERRED EMBODIMENTS

The local application of C20 or C22 acids has been found to promote wound healing. This is true both of animals which have not been otherwise treated and also true of animals which have been treated with antiinflammatory agents such as a salicylate, hydrocortisone, prednisone, indomethacin, mefenamic acid and the like. These compounds normally retard healing and C20 and C22 acids reverse this action.

The following is one method of preparing the novel C20 and C22 acids of the present invention. In the synthesis selected, beta ionone is first converted to an aldehyde having 16 carbon atoms and this is reacted with triethylphosphonocrotonate to produce the C20 ethyl ester and this is hydrolyzed to the desired C20 acid. It is also possible to go directly from the C12 aldehyde to the C20 ester by employing a phosphono compound having eight carbon atoms with conjugated double bonds. One route for preparing the C22 acid is through the C20 acid.

PREPARATION OF BETA C12 ACID

At 0° pass 84 grams of chlorine gas into 400 ml of 10M sodium hydroxide solution. To which, at room temperature, add 64 grams of beta ionone. Stir for three hours. Add 80 ml of methanol and maintain the temperature below 85° C by adding crushed ice and then bring the pH to about 4 by adding phosphoric acid. Cool to room temperature and the beta C12 acid will rise to the surface and can be filtered with the aid of suction. The crude acid is then dissolved in 20% aqueous sodium hydroxide solution and extracted with ether. The aqueous solution is acidified with phosphoric acid and again extracted with ether. The ether extract is dried with anhydrous magnesium sulfate. The ether is evaporated and the acid is recrystallized from 70% methanol solution to provide the purified C12 acid.

PREPARATION OF C12 ALCOHOL

Ten grams of lithium aluminum hydride is placed in a 3 necked flask under a nitrogen atmosphere and 50 ml of anhydrous ethyl ether is added and stirred with a magnetic stirrer at −15° C. Dissolve 50 grams of the C12 acid previously pepared in anhydrous ether and add slowly into the flask containing the lithium aluminum hydride. The temperature should be maintained below minus 10° C. After all of the acid has been added, the temperature can be allowed to rise to room temperature and kept at this temperature for 1 hour. The mixture is then cooled to 0° and 1N sulphuric acid is added until bubbles cease to form. The temperature should be maintained below 5° C. The reaction mixture is filtered and the precipitate washed with ether. The ether layer is separated and washed with water and is then dried with anhydrous magnesium sulfate and the ether evaporated. The yield is about 93% of theory.

PREPARATION OF C12 ALDEHYDE

In the following reaction, activated manganese dioxide is used which can be prepared either by the method of Attenburrow et al J. Chem. Soc. 1094 (1952) or Carpino, J. Org. Chem. Vol. 35 No. 11 (1970) 3971.

About 50 grams of the C12 alcohol in ether solution is placed in a dropping funnel attached to a two-liter flask. 500 grams of activated manganese dioxide and 1000 ml of anhydrous carbon tetrachloride are placed in the flask and stirred. The C12 alcohol solution is now slowly run into the manganese dioxide suspension and stirring is continued at room temperature for two hours after all of the alcohol has been added. The mixture is filtered and washed with carbon tetrachloride and the extract is then dried and evaporated. The yield is about 95% of theory.

PREPARATION OF C16 ESTER

Weigh 47 grams of a sodium hydride in oil dispersion (57% NaH) and place it in a two liter flask. Wash with anhydrous ether. Add 1000 ml of anhydrous tetrahydrofuran (THF) and cool to zero. One then places 140 grams of triethylphosphonocrotonate in a dropping funnel and adds it dropwise to the sodium hydride suspension with stirring. Stirring is continued at zero degrees for ½ hour after all the crotonate has been added.

About 50 grams of the C12 aldehyde dissolved in THF is now slowly added and warmed to room temperature and allowed to stand at room temperature over ½ hour. The mixture is then cooled to zero and one adds a saturated sodium chloride solution to destroy the excess of sodium hydride. The mixture is now extracted with petroleum ether and the extract dried to evaporate the solvent, yielding the desired ester.

PREPARATION OF C16 ACID

The ester is hydrolyzed by refluxing it in a 10% potassium hydroxide-ethanol solution under nitrogen for 4 hours. The mixture contains 50 grams of the ester, 50 grams of potassium hydroxide, 300 ml of water and 200 ml of ethanol. After the hydrolysis is completed, acidify the mixture. The acid can be extracted with ethyl ether.

PREPARATION OF C20 AND C22 ACIDS

The detailed procedure for obtaining the C20 from the C16 acid is not given since the reactions are substantially the same as outlined above. The C16 acid recovered from the last step is converted to the alcohol, utilizing lithium aluminum hydride and this is converted to the corresponding aldehyde utilizing magnesium dioxide as described above. The aldehyde now is reacted with triethylphosphonocrotonate to produce the C20 ethyl ester and this in turn is hydrolyzed as described above to produce the C20 acid of the present invention. The C22 acid can be prepared from the C20 acid by using the above method and employing triethylphosphonoacetate.

C20 or C22 acids can be applied in the form of an ointment, as a solution in oil or as a powder. In each instance a concentration of about 1% has been found suitable although larger or smaller concentrations may be used. Below about ½%, the effectiveness falls off and increasing the concentration from 1 to 2% increases the effectiveness only slightly. Therefore a concentration of about 1%, whether in an ointment, oil solution or powder is about optimum.

Suitable oil carriers include physiologically acceptable oils in which the acid is soluble such as isopropyl myristate, corn oil, cottonseed oil and the like. Powder can be prepared utilizing the C20 or C22 acid crystals by grinding the crystals with a suitable inert carrier such as talc. C20 or C22 acid can be combined with any of the usual ointment bases used in pharmacy. One suitable base is known as NIB (non-ionic base) developed by the University of California School of Pharmacy having the following approximate composition:

| | |
|---|---|
| Cetyl alcohol | 6% |
| Stearyl alcohol | 6 |
| White petrolatum | 14 |
| Liquid petrolatum | 20 |
| Methyl paraben | 0.15 |
| Propyl parben | 0.06 |
| Polysorbate 80 | 1.5 |
| Polyoxyl 40 stearate | 5 |
| Propylene glycol | 2 |
| Purified water | q.s. 100% |

Grindlay and Waugh (Arch. Surg. 63, 288 (1951) used granuloma formation induced by polyvinyl sponge to study tissue regeneration. Since then this method has been used as a standard method to study wound healing. Dunphy and his associates (Ann. N.Y. Acad. Sci. 86, 943 (1960) have pointed out that the repairment of connective tissue is the most basic feature in wound healing, and they used granuloma formation techniques in their many wound healing studies.

This method involves subcutaneous implantation of cotton-pellets and measuring the size of the granuloma induced after a few days. Anti-inflammatory agents reduce the size or weight of granuloma as compared with that of the control. Those compounds which promote healing increase the size or weight of the granuloma.

Growth of granulation tissue into cotton-pellets was induced by subcutaneous implantation at two symmetrical dorsolateral sites of Sprague-Dawley male rats weighing 120 ± 5 g under ether anesthesia.

The cotton-pellet implanted on the right side contains the compound under test and the cotton-pellet implanted on the left side serves as the control. The compound was introduced to the pellet as its ether solution. The ether was completely evaporated before implantation. On the seventh day after implantation, the animals were killed with ether and the body weights were taken. The granulomas were carefully removed and weighed rapidly on a torsion balance. After drying in an oven at 65° C for 48 hours the dried slices were weighed. The following results were obtained.

| EFFECT OF 3',7'-DESMETHYL RETINOIC ACID VINYLOGS ON COTTON-PELLET INDUCED GRANULOMA IN RATS | | | | | | | |
|---|---|---|---|---|---|---|---|
| | | | Granuloma Wet. Wt. mg. | | Granuloma Dry Wt. mg. | | |
| Group | No. of Animals | Acids Applied | Expt. | Control | Expt. | Control | |
| I | 6 | A | 238.6±12.1 | | 29.0±2.1 | | |
| | | | 220.5±12.2 | 1.1 | 27.2±2.1 | 1.1 | |
| II | 14 | B | 331.1±14.8 | | 43.1±2.6 | | |
| | | | 208.8± 5.9 | 1.5 | 25.5±1.5 | 1.7 | |
| III | 43 | C | 430.2± 8.1 | | 68.9±1.5 | | |
| | | | 205.0± 2.7 | 2.2 | 23.9±0.9 | 2.9 | |
| IV | 30 | D | 373.9± 8.6 | | 60.5±1.6 | | |
| | | | 202.9± 4.6 | 1.8 | 24.9±1.2 | 2.4 | |
| A Acid: | 2, 6, 6, -Trimethyl-1-(6'-carboxy-hexa-1', 3',5'trienyl) cyclohex-1-ene. | | | | | | |
| B Acid: | 2, 6, 6, -Trimethyl-1-(8'-carboxy-octa-1',3',5'7'tetraenyl) cyclohex-1-ene or 3',7'-desmethyl retinoic acid. | | | | | | |
| C Acid: | 2, 6, 6, -Trimethyl-1-(10'-carboxy-deca-1',3',5',7',9' -pentaenyl) cyclohex-1-ene. | | | | | | |
| D Acid: | 2, 6, 6, -Trimethyl-1-(12'-carboxy-dodeca-1',3',5',7',9',11'hexaenyl) cyclohex-1-ene. | | | | | | |

It is believed apparent from the foregoing that the C20 and C22 acids of the present invention (Acid C and D in the table) are highly effective for wound healing and are much more effective than the homologs having 16 or 18 carbon atoms. The C20 acid is somewhat more effective than the C22 acid.

Further tests established that the C20 and C22 acids are not toxic or at least not as toxic as retinoic acid. Retinoic acid inhibits embryonic chick tibia growth while C20 and C22 do not. Retinoic acid, at higher dosage (4 mg/100g rat) inhibits growth. The C20 at even higher dosages (8 mg/100g rat) does not inhibit growth.

I claim:

1. An acid 2,6,6,-Trimethyl-1-(10'-carboxy-deca-1',3',5',7',9'-pentaenyl) cyclohex-1-ene.